United States Patent [19]

Gedridge, Jr.

[11] Patent Number: 5,326,425
[45] Date of Patent: Jul. 5, 1994

[54] PREPARATION OF TERTIARYBUTYLDIMETHYLANTIMONY AND USE THEREOF

[75] Inventor: Robert W. Gedridge, Jr., Ridgecrest, Calif.

[73] Assignee: The United States of America as represented by the Secretary of the Navy, Washington, D.C.

[21] Appl. No.: 34,792

[22] Filed: Jan. 28, 1993

[51] Int. Cl.$^5$ .......................... C30B 25/02; C07F 9/90
[52] U.S. Cl. ...................................... 117/104; 556/70; 117/939; 117/953
[58] Field of Search .................. 556/70; 156/610, 613, 156/614

[56] References Cited

U.S. PATENT DOCUMENTS 4,517,047  5/1985  Chang et al. .................. 156/610
4,904,616  2/1990  Bohling et al. .................. 437/81

OTHER PUBLICATIONS

Chen et al., Appl. Phys. Lett., vol. 61, No. 2, pp. 204–206 (1992).

Cao et al., J. Electron, Mater., vol. 21, pp. 583–588 (1992).

*Primary Examiner*—José G. Dees
*Assistant Examiner*—Porfirio Nazario-Gonzalez
*Attorney, Agent, or Firm*—John L. Forrest, Jr.; Melvin J. Sliwka; Stuart H. Nissim

[57] ABSTRACT

The new compound tertiarybutyldimethylantimony is prepared by reacting an antimony trihalide $SbX_3$ with the tertiarybutyl Grignard reagent $((CH_3)_3C)MgX$, treating the resulting product with the methyl Grignard reagent $(CH_3)MgX$, where X is a halide, and recovering tertiarybutyldimethylantimony from the reaction mixture. The reaction is preferably carried out by a one pot synthesis in a suitable solvent such as diethyl either using approximately one equivalent of $((CH_3)_3C)MgX$ in relation to the $SbX_3$ at about $-50°$ C., followed by treatment with approximately two equivalents of $(CH_3)MgX$ in relation to the $SbX_3$ at about $0°$ C. The tertiarybutyldimethylantimony is used as a precursor in forming antimony-containing semiconductor material by chemical vapor deposition.

14 Claims, No Drawings

PREPARATION OF TERTIARYBUTYLDIMETHYLANTIMONY AND USE THEREOF

BACKGROUND OF THE INVENTION

The present invention relates to the process to prepare tertiarybutyldimethylantimony, $((CH_3)_3C)(CH_3)_2Sb$, and its use in chemical vapor deposition processes to produce antimony-containing semiconductor materials.

A variety of semiconductor systems containing antimony have been investigated for applications in infrared detectors, high speed devices, optoelectric devices, and motion and position sensors.

Antimony-containing binary materials, e.g. InSb and GaSb, as well as ternary and quaternary materials, e.g. InAsSb and InAsSbBi, have been grown heteroepitaxially by organometallic vapor phase epitaxy (OMVPE), a high throughput technique for the production of high quality semiconductor materials from organometallic precursors such as organoantimony compounds.

Certain semiconductor materials have been grown by OMVPE using trimethylantimony or triethylantimony as the organoantimony source compound. Attempts at low growth temperatures resulted in significant problems due to the incomplete pyrolysis of these organoantimony compounds.

An alternative organoantimony precursor for OMVPE is needed which has a lower pyrolysis temperature than the above trimethyl and triethyl antimony compounds. It is also important that such alternative organoantimony precursor pyrolyze with minimal unintentional impurity incorporation. Recently, triisopropylantimony, $((CH_3)_2CH)_3Sb$, was used to grow epitaxial InSb films at temperatures as low as 300° C. However, triisopropylantimony has a low vapor pressure in comparison to trimethylantimony and very low film growth rates resulted. An organoantimony precursor with a higher vapor pressure and a low decomposition temperature is still needed.

The availability of alternative Sb source compounds for OMVPE could greatly enhance the development of antimony-containing semiconductor materials. Development of new Sb source compounds for chemical vapor deposition processes is of interest for lowering the film-growth temperature of Sb-containing semiconductor materials and altering the chemistry to minimize unintentional impurities.

One object of the invention is the provision of an improved organoantimony source compound for antimony-containing semiconductor materials.

Another object is to provide an organoantimony precursor for OMVPE for the production of antimony-containing semiconductor materials having a higher vapor pressure and a lower decomposition temperature than organoantimony presursors heretofore used.

Still another object is the provision of a novel organoantimony precursor which pyrolyses with minimal unintentional impurity incorporation into the antimony-containing semiconductor material.

A still further object is to provide a process for preparing such antimony source compound or precursor for production of antimony-containing semiconductor materials.

Yet another object is the provision of a process of forming an antimony-containing semiconductor material by chemical vapor deposition, using an improved organoantimony source compound.

SUMMARY OF THE INVENTION

The above objects and advantages can be achieved according to the invention by the provision of the new compound tertiarybutyldimethylantimony, $((CH_3)_3C)(CH_3)_2Sb$. This compound can be conveniently prepared in a one-pot synthesis and isolated by reacting an antimony trihalide $(SbX_3)$ with the tertiarybutyl Grignard reagent $((CH_3)_3C)MgX$; treating the resulting product with the methyl Grignard reagent $(CH_3)MgX$, where X is a halide; and recovering tertiarybutyldimethylantimony from the reaction mixture.

The reaction is carried out in an organic solvent using approximately one equivalent of $((CH_3)_3C)MgX$ in relation to the $SbX_3$, at or below about $-50°$ C., followed by treatment with approximately two equivalents of $(CH_3)MgX$ in relation to the $SbX_3$ at or above about $0°$ C.

Also, according to the invention, an improved process is provided for forming antimony-containing semiconductor materials using chemical vapor deposition. In the process tertiarybutyldimethylantimony is used as the source of antimony.

DETAILED DESCRIPTION OF THE INVENTION AND PREFERRED EMBODIMENTS

The new compound tertiarybutyldimethylantimony is prepared according to the reaction scheme noted below:

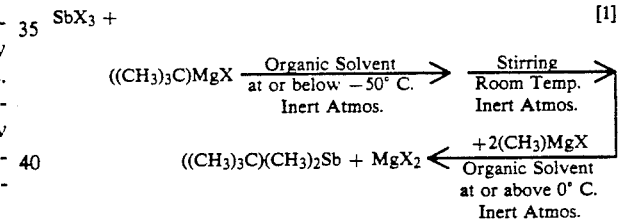

In preferred practice, an antimony trihalide, $SbX_3$, is reacted with about one equivalent of tertiarybutyl Grignard reagent $((CH_3)_3C)MgX$ at or below about $-50°$ C.; warmed to room temperature; cooled to about $0°$ C. for the addition of about two equivalents of methyl Grignard reagent $(CH_3)MgX$, where $X=$a halide, at about $0°$ C., in a suitable solvent; under an inert atmosphere, All preparation, isolation, and purification of the air-sensitive product is carried out using inert-atmosphere techniques.

In the above reactions, a 1:1 molar ratio of the tertiarybutyl Grignard reagent to the antimony trihalide is employed. However, it is preferred to employ a small excess (about 5%) of the tertiarybutyl Grignard reagent in the event that the tertiarybutyl Grignard regent is not pure. In the above reactions, a 2:1 molar ration of the methyl Grignard reagent to the antimony trihalide is employed. However, it is here also preferred to employ a small excess (about 5%) of the methyl Grignard reagent in the event that the methyl Grignard reagent is not pure.

Solvents used during synthesis must be thoroughly free of oxygen or water. While diethyl ether is the preferred solvent in which to carry out the reactions above, other oxygen and water-free organic solvents, e.g. tetrahydrofuran, other ethereal solvents, or some combination of solvents, can be employed.

The reactions as illustrated in equations (1) above, for the production of tertiarybutyldimethylantimony are commenced at low temperatures of about −78° C. to about −50° C., preferably about −50° C., for the addition of the tertiarybutyl Grignard reagent. If the tertiarybutyl Grignard reagent is added at temperatures above −50° C., more of the unwanted ditertiarybutylmethylantimony and tritertiarylbutylantimony side products will form. The addition of the methyl Grignard reagent is at temperatures of 0° C. or higher, e.g. to about 25° C., preferably about 0° C. After the addition of the methyl Grignard reagent the slurry is allowed to warm to room temperature and stirred at least overnight, preferably about 48 hours.

After the addition of the Grignard reagents is complete to form the tertiarybutyldimethylantimony, distilled water that has been deoxygenated by a series of freeze-thaw degas cycles, or any other appropriate deoxygenating method, is slowly added to separate the magnesium salts and other water soluble salts from the tertiarybutyldimethylantimony in the organic layer. This exothermic step should be performed under cooled condition, preferably at about 0° C.

After the addition of the deoxygenated distilled water, the slurry is stirred at least overnight, preferably at least 24 hours, and allowed to settle. The two layers are then separated and the upper organic layer with the tertiarybutyldimethylantimony is transferred to a dry clean Schlenk flask that has been charged with a drying agent such as anhydrous $MgSO_4$ under an inert atmosphere. Other suitable drying reagents, e.g. anhydrous $CaCl_2$ or Grignard reagents, can be employed in place of anhydrous $MgSO_4$. After drying the organic layer over anhydrous $MgSO_4$ for several hours or more, the organic layer is filtered under an inert atmosphere and the solvent is fractionally removed by distillation. Tertiarybutyldimethylantimony is then collected by fractional vacuum distillation and purified by fractional vacuum distillation.

A preferred reaction scheme is noted below:

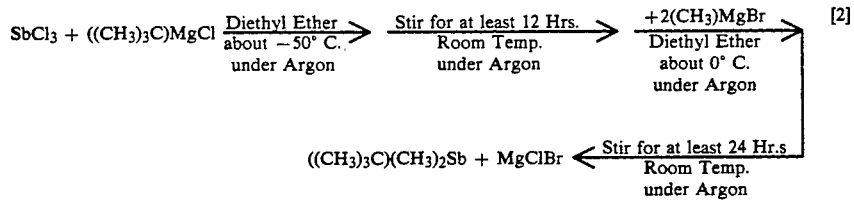

Pressure is not a critical factor in carrying out reactions (1) and (2) above, and generally ambient pressure is employed, although higher or lower pressures can be utilized in the preparation of tertiarybutyldimethylantimony.

Tertiarybutyldimethylantimony is a colorless liquid at room temperature. Tertiarybutyldimethylantimony is extremely air-sensitive and requires its preparation, isolation and purification under an inert atmosphere, e.g. argon, nitrogen, helium. Tertiarybutyldimethylantimony has a melting point around 12°-13° C., and a vapor pressure approximately 3.6 torr (mm Hg) at 25° C.

In the above reactions (1) and (2), lithium reagents, e.g. tertiarybutyl lithium or methyl lithium can be employed in place of the Grignard reagents, e.g. tertiarybutyl magnesium halide or methylmagnesium halide. However, such Grignard reagents are the preferred reactants for the reactions with an antimony trihalide.

The following are examples of preparation of the novel organoantimony compound of the invention.

EXAMPLE 1

Tertiarybutyldimethylantimony, $((CH_3)_3C)(CH_3)_2Sb$, was prepared by a one pot reaction of $SbCl_3$ with one equivalent of tertiarybutyl Grignard reagent followed by two equivalents of methyl Grignard reagent.

To a solution of 148.6 g (651.5 mmol) of $SbCl_3$ (99.99% pure by metal basis) in 800 mL of dry deoxygenated diethyl ether at −50° C. was added dropwise (drop time=3 hours) with vigorous stirring 342 mL (2.0M diethyl ether, 682 mmol) of tertiarybutyl magnesium chloride. After the addition was complete, the slurry was stirred at −50° C. for 1 hour. Then the slurry was allowed to warm to room temperature slowly (about 2 hours time) and stirred at room temperature for an additional 1.5 hours. The slurry was then cooled to 0° C. and 500 mL (2.7M diethyl either, 1350 mmol) of methyl magnesium bromide in was added dropwise (drop time=3 hours) to the slurry at 0° C. The slurry was allowed to reach room temperature and stirred at room temperature for 24 hours then refluxed for 3 hours. The slurry was cooled to 0° C. and 500 mL of deoxygenated distilled water was added dropwise (drop time=2 hours) to the slurry with stirring. A condenser was used to prevent the distillation of the diethyl ether from this exothermic step. The slurry was stirred 24 hours then allowed to settle. The upper organic layer was transferred to a Schlenk flask with anhydrous $MgSO_4$ and stirred 24 hours at room temperature. The slurry was filtered and the diethyl ether solvent was removed by fractional distillation. Tertiarybutyldimethylantimony was collected in a liquid nitrogen trap down to 6 torr using a 55° C. water bath. The tertiarybutyldimethylantimony was purified by fractional vacuum distillation at 44° C. at 11 torr (87.7 g, 64% yield based on $SbCl_3$). The tertiarybutyldimethylantimony was purified by fractional vacuum distillation two more times (55° C. at 20 torr and 63° C. at 30 torr). Melting point is about 12°-13° C. Tertiarybutyldimethylantimony was characterized by $^1H$ and $^{13}C$ NMR spectroscopy. Elemental Analysis was carried out. Analysis calculated for $C_6H_{15}Sb$: C, 34.49; H, 7.24; Sb, 58.27. Found: C, 34.63; H, 7.20; Sb, 57.50.

EXAMPLE 2

To a solution of 206.331 g (904.548 mmol) of $SbCl_3$ (99.99% pure by metal basis) in 750 mL of dry deoxygenated diethyl ether at −55° to −50° C. was added dropwise (drop time=3½ hours) with vigorous stirring 475 mL (2.0M diethyl ether, 950 mmol) of tertiarybutyl magnesium chloride. After the addition was complete, the slurry was allowed to warm to room temperature slowly (about 2 hours time) and stirred at room temperature overnight. The slurry was then cooled to 0° C. and 660 mL (3.0M diethyl either, 1980 mmol) of methyl magnesium bromide in was added dropwise (drop time=3 hours) to the slurry at 0° C. The slurry was allowed to reach room temperature and stirred at room temperature for 48 hours. The slurry was cooled to 0° C. and 500 mL of freeze/thaw deoxygenated distilled water was added dropwise (drop time=6 hours) to the slurry with stirring. A condenser was used to prevent the distillation of the diethyl ether from this exothermic step. The slurry was stirred 2 hours then allowed to settle. The diethyl ether solvent was removed by fractional distillation. After removal of the diethyl ether solvent, 25 mL of tertiarybutyl magnesium chloride, as a drying agent was added and then heated to 55° C. and stirred for about 2 hours. Tertiarybutyldimethylantimony was collected in a liquid nitrogen trap down to 2 torr using a 65° C. water bath. The tertiarybutyldimethylantimony was heated to 55°-60° C. in a water bath down to 50 torr for 1½ hours. The tertiarybutyldimethylantimony was purified by fractional vacuum distillation (50° C. at 28 torr). Obtained 141.556 g, 75% yield based on $SbCl_3$. Melting point is about 12°-13° C. Tertiarybutyldimethylantimony was characterized and confirmed 99% pure by $^1H$ NMR spectroscopy.

Tertiarybutyldimethylantimony, $((CH_3)_3C)(CH_3)_2Sb$, can be used as an alternative precursor to the OMVPE growth of antimony-containing, e.g. III/V Sb-containing, semiconductor materials. Tertiarybutyldimethylantimony can also be used to introduce Sb as a dopant in II/VI and IV semiconductor materials. Tertiarybutyldimethylantimony can decompose at lower temperatures than trimethylantimony due to the reduced bond strength of the $((CH_3)_3C)$—Sb bond. Tertiarybutyldimethylantimony is an alternative Sb source compound with a useful vapor pressure that can be used at lower film growth temperatures and pyrolyses more efficiently at higher growth temperatures than trimethylantimony.

III/V antimony-containing semiconductor materials can be binary (2-element), ternary (3-element) or quaternary (4-element) semiconductor materials containing at least one element from group IIIB and at least one element from group VB of the periodic table, at last one of such elements from group VB being antimony.

Tertiarybutyldimethylantimony is used to introduce antimony into semiconductor materials following methods known in the art, generally described as follows: Hydrogen or some other carrier gas, e.g., helium, nitrogen, is bubbled through liquid tertiarybutyldimethylantimony in a container. The hydrogen transports the tertiarybutyldimethylantimony in vapor phase into a reactor for chemical vapor deposition (e.g., OMVPE). The vapor stream comes into contact with a heated substrate, which can be any semiconductor substrate such as Si, GaAs, InSb, GaP, InP or InAs. This can be done at low, atmospheric or high pressures.

In case of a binary semiconductor, containing antimony, for example, there are two lines entering the reaction zone each with a gas saturated with a precursor of the two elements, one of which is tertiarybutyldimethylantimony. Such gases contact the heated substrate and deposit a semiconductor on the substrate. Where tertiarybutyldimethylantimony is used as a precursor to introduce antimony as a dopant into semiconductor materials, substantially the same process as noted above is employed, but at a low concentration of the tertiarybutyldimethylantimony in the gas phase, so that the antimony is not a major component of the resulting semiconductor compound, but is present in sufficient concentration to provide suitable desired electrical properties.

EXAMPLE 3

Using a horizontal OMVPE reactor, InSb was grown using tertiarybutyldimethylantimony and trimethylindium under a variety of growth conditions over a temperature range of 360° to 475° C., a pressure range of 215 to 660 torr, and Group V/Group III ratios of 1.3 to 24. The flow rates of trimethylindium at 10° C. were varied from 27 to 200 SCCM. The flow rates of tertiarybutyldimethylantimony at 20° C. (P=5.4 torr) were varied from 42 to 200 SCCM. Detailed descriptions and results of these growth studies can be found in an article by R. M. Biefeld and R. W. Gedridge, Jr. entitled The growth of InSb using triisopropylantimony or tertiarybutyldimethylantimony and trimethylindium, Journal of Crystal Growth, 124 (1992) pages 150–157.

From the foregoing, it is seen that the present invention provides for the preparation and isolation of the novel compound tertiarybutyldimethylantimony, $((CH_3)_3C)(CH_3)_2Sb$.

Tertiarybutyldimethylantimony is an alternative improved antimony precursor for forming antimony-containing semiconductor materials using chemical vapor deposition techniques, e.g. organometallic vapor phase epitaxy. In the process tertiarybutyldimethylantimony is used as a source of antimony. The process can be used in forming III/V antimony-containing semiconductor materials, and can also be used to introduce antimony as a dopant in II/VI and IV semiconductor materials.

Since various changes and modifications can be made in the invention without departing from the spirit of the invention, the invention is not to be taken as limited except by the scope of the appended claims.

What is claimed is:

1. The compound having the formula $((CH_3)_3C)(CH_3)_2Sb$.

2. A process for preparing the compound having the formula $((CH_3)_3C)(CH_3)_2Sb$ which comprises:
   A.) reacting $SbX_3$ with $((CH_3)_3C)MgX$;
   B.) treating the resulting product with $(CH_3)MgX$; and,
   C.) recovering $((CH_3)_3C)(CH_3)_2Sb$ from the reaction mixture, where X is a halide.

3. The process of claim 2, employing approximately one equivalent of $((CH_3)_3C)MgX$, and approximately two equivalents of $(CH_3)MgX$, in relation to the $SbX_3$.

4. The process of claim 3, the reaction with $((CH_3)_3C)MgX$, taking place at a temperature not higher than $-50°$ C., and the reaction with $(CH_3)MgX$, taking place at a temperature of 0° C. or higher.

5. The process of claim 2, the reactions and recovery taking place in an inert atmosphere.

6. The process of claim 2, the reactions taking place in an organic solvent.

7. The process of claim 2, the recovering step including adding deoxygenated water to the final reaction mixture to separate the water soluble salts from the organic layer containing the $((CH_3)_3C)(CH_3)_2Sb$ product and removing the solvent from the organic solvent layer.

8. The process of claim 3, the reaction with $((CH_3)_3C)MgX$ taking place at a temperature ranging from about −78° C. to about −50° C., and the treatment with (CH$_3$)MgX taking place at a temperature ranging from about 0° C. to about 25° C., and employing a small excess of ((CH$_3$)$_3$C)MgX and a small excess of (CH$_3$)MgX.

9. The process of claim 3, the reaction with ((CH$_3$)$_3$C)MgX taking place at about −50° C., and the reaction with (CH$_3$)MgX taking place at about 0° C., and employing a small excess of ((CH$_3$)$_3$C)MgX and a small excess of (CH$_3$)MgX.

10. A process or preparing the compound having the formula (CH$_3$)$_3$C)(CH$_3$)$_2$Sb which comprises:
   A.) reacting antimony trihalide with approximately one equivalent of tertiarybutyl magnesium halide in relation to the antimony trihalide at about −50° C. in an oxygen and water free organic solvent;
   B.) stirring the resulting reaction product at room temperature for at least 12 hours;
   C.) reacting the resulting reaction product with two equivalents of methyl magnesium halide in relation to the antimony trihalide at approximately 0° C. in said solvent;
   D.) stirring the resulting reaction product at room temperature for at least 12 hours;
   E.) adding water to the final reaction mixture to separate the water soluble salts from the organic solvent layer containing the tertiarybutyldimethylantimony product;
   F.) removing the solvent from the organic solvent layer by distillation; and
   G.) recovering the tertiarybutyldimethylantimony product; wherein the entire process is carried out in an inert atmosphere.

11. The process of claim 10, the antimony trihalide and the tertiarybutyl magnesium halide being the corresponding chlorides, the methyl magnesium halide being the corresponding bromide, and the solvent being diethyl ether.

12. The process of claim 10, using a small excess of said tertiarybutyl magnesium halide and a small excess of said methyl magnesium halide, and the water added to the final reaction mixture is distilled deoxygenated water.

13. In a process of forming an antimony-containing semiconductor material by chemical vapor deposition, the improvement comprising using ((CH$_3$)$_3$C)(CH$_3$)$_2$Sb as a source of antimony.

14. The process of claim 13, which comprises bubbling a carrier gas thorough liquid ((CH$_3$)$_3$C)(CH$_3$)$_2$Sb, and transporting the ((CH$_3$)$_3$C)(CH$_3$)$_2$Sb with the carrier gas to a heated substrate and depositing Sb from said ((CH$_3$)$_3$C)(CH$_3$)$_2$Sb, and additional elements on said substrate from groups selected from Groups II, III, V and VI of the periodic table to form III/V Sb-containing semiconductor materials or to provide Sb as a dopant in II/VI and IV semiconductor materials.

* * * * *